(12) United States Patent
Fago

(10) Patent No.: US 6,511,459 B1
(45) Date of Patent: Jan. 28, 2003

(54) SYRINGE PLUNGER HAVING AN IMPROVED SEALING ABILITY

(75) Inventor: Frank M. Fago, Mason, OH (US)

(73) Assignee: Mallinckrodt Inc., St. Louis, MO (US)

( * ) Notice: Subject to any disclaimer, the term of this patent is extended or adjusted under 35 U.S.C. 154(b) by 16 days.

(21) Appl. No.: 09/676,143

(22) Filed: Sep. 29, 2000

(51) Int. Cl.$^7$ .............................................. A61M 5/178
(52) U.S. Cl. ...................................... 604/181; 604/122
(58) Field of Search ................................ 604/181, 110, 604/187, 218, 183, 227, 72, 573, 82; 600/579

(56) References Cited

U.S. PATENT DOCUMENTS

| | | | |
|---|---|---|---|
| 1,453,418 A | 5/1923 | Tessmer | |
| 2,895,773 A | 7/1959 | McConnaughey | 309/23 |
| 3,373,999 A | 3/1968 | Jepsen | 277/193 |
| 3,535,068 A | 10/1970 | Larson | 128/218 |
| 3,581,956 A | 6/1971 | Reid | 222/386 |
| 5,007,904 A | 4/1991 | Densmore et al. | 604/228 |
| 5,236,420 A | 8/1993 | Pfleger | 604/122 |
| 5,397,313 A | 3/1995 | Gross | 604/218 |
| 5,496,285 A | 3/1996 | Schumacher et al. | 604/218 |
| 5,531,255 A | 7/1996 | Vacca | 141/285 |
| 5,586,975 A | 12/1996 | Tanaka et al. | 604/89 |
| 5,637,092 A * | 6/1997 | Shaw | 604/110 |
| 5,735,825 A | 4/1998 | Stevens et al. | 604/218 |
| 5,785,682 A * | 7/1998 | Grabenkort | 604/82 |
| 5,891,052 A * | 4/1999 | Simmons | 604/573 |
| 5,938,637 A * | 8/1999 | Austin et al. | 604/72 |
| 6,050,957 A * | 4/2000 | Desch | 600/579 |
| 6,086,569 A * | 7/2000 | Schweizer | 604/227 |
| 6,213,980 B1 * | 4/2001 | Colburn et al. | 604/183 |
| 6,213,985 B1 * | 4/2001 | Niedospia, Jr. | 604/218 |
| 6,361,524 B1 * | 3/2002 | Odell et al. | 604/187 |
| 6,368,303 B1 * | 4/2002 | Caizza | 604/110 |

* cited by examiner

Primary Examiner—Teresa Walberg
Assistant Examiner—L Fastovsky
(74) Attorney, Agent, or Firm—Wood, Herron & Evans, L.L.P.

(57) ABSTRACT

A plunger is provided for a syringe that includes a pressure relief mechanism that exhausts any fluid trapped in the chamber between sealing flanges carried by the plunger when the plunger is advanced to dispense fluid from the syringe. The contact pressure between the barrel-contacting surface of the rearmost sealing flange nearest the access opening of the syringe barrel is weakened relative to the contact pressure provided by the barrel-contacting surface of the sealing flange that isolates the fluid within the barrel. The contact pressure of the rearmost sealing flange may be lessened by either reducing its radial diameter relative to the radial diameter of the other sealing flange, removing an underlying portion of the plunger, or configuring the rearmost sealing flange as deflectable sealing lip.

63 Claims, 3 Drawing Sheets

SYRINGE PLUNGER HAVING AN IMPROVED SEALING ABILITY

FIELD OF THE INVENTION

This invention relates to syringes, and more particularly, to a plunger having an improved sealing ability for use with a syringe.

BACKGROUND OF THE INVENTION

Syringes are devices routinely employed for providing a quantity of a medical liquid to a patient, typically into the patient's arteriovenous system, and for dispensing liquids in other non-medical applications. Syringes are traditionally configured with a tubular barrel for holding the liquid, a plunger within the barrel, an access opening for the plunger at a proximal end of the barrel, and a smaller discharge outlet at a distal end of the barrel. The plunger has a proximal portion adapted to receive a dispensing force, a central section with sealing flanges, and a distal head that contacts the liquid within the barrel. During a dispensing procedure, a dispensing force moves the plunger in a distal direction along the longitudinal length of the barrel, if the magnitude of the dispensing force is sufficient, to urge the liquid contained in the barrel through the discharge outlet. The sufficiency of the dispensing force depends, among other factors, upon the viscosity of the liquid held by the barrel.

Plungers usually carry two annular sealing flanges of substantially identical dimension and in a spaced relationship that extend about the circumference of an outer surface of the plunger. Each flange has a barrel-contacting sealing surface configured to compressively engage the interior of the barrel. An annular chamber is defined in the space bounded by the adjacent sealing flanges, the cylindrical side wall of the plunger and the interior cylindrical surface of the barrel. During a dispensing procedure, the distal sealing flange exerts a contact pressure against the interior wall of the barrel sufficient to prevent unwanted leakage of the liquid past the plunger in a proximal direction. The proximal sealing flange is present to ensure proper alignment of the plunger during a dispensing procedure and to prevent the passage of air during when the syringe is aspirated to, for example, fill the interior of the barrel forward of the plunger with liquid.

As the dispensing force advances the plunger, the liquid in the barrel exerts a significant hydrostatic pressure against a distal surface of the plunger. The plunger is formed of a resilient material that responds to the hydrostatic pressure by compressing along its longitudinal axis. The axial compression is accommodated by an outward distention of the plunger body. The sealing flanges likewise move radially outward so that the contact pressure is enhanced between the barrel-contacting sealing surface of the distal sealing flange and the interior of the barrel. The enhanced contact pressure offsets the increased hydrostatic pressure exerted by the liquid against the distal sealing flange and preserves the integrity of the fluid-tight barrel-contacting engagement. However, the outward distention of the side walls also reduces the volume of the annular chamber.

The annular chamber is normally occupied by a compressible fluid, such as air, that can accommodate a change in volume without supplying a significant opposing force against the contact pressure. In certain situations, however, a quantity of liquid may pass the distal sealing flange and become trapped in the annular chamber nearest to the distal sealing flange prior to either initiating or completing the dispensing procedure. For example, liquid may become trapped in the annular chamber when the syringe is filled or if the plunger cants during the dispensing procedure. Liquids are relatively incompressible fluids that occupy roughly a constant volume independent of an applied external pressure.

If a significant quantity of liquid is trapped in the annular chamber, the contact pressure exerted against the interior of the barrel by the sealing surfaces of the sealing flanges will be reduced. In particular, the distal sealing flange may actually exert a lesser contact pressure against the interior of the barrel than the proximal sealing flange. During the dispensing operation, the contact pressure between the distal sealing flange and the interior of the barrel cannot increase commensurate with the axial compression due to the presence of the incompressible trapped liquid. As a result, the sealing ability of the distal sealing flange may be compromised.

If the distal sealing flange loses contact with the interior of barrel, the highly pressurized liquid within the barrel will rush through the newly-created gap. The proximal sealing flange is not configured to resist the flow of highly pressurized liquid and readily yields to the leaking liquid, which exits past the plunger in a proximal direction toward the access opening. When such "blow-by" events occur, significant quantities of liquid can stream past the plunger. Among the undesirable side effects of blow-by, the patient will receive less liquid per unit distance of plunger movement than the prescribed dosage. If the syringe is recycled to perform multiple dispensing operations, the likelihood of a blow-by event increases with each subsequent dispensing operation.

Liquid may be dispensed in an precise fashion over a lengthy duration with the assistance of a power injector. Power injectors utilize a motor-driven plunger drive adapted to engage and continuously advance the plunger for incrementally dispensing the contents of the syringe over an extended time according to predetermined injection parameters such as flow rate, volume, duration, and time. Power injectors are commonly used for carrying out extended infusions of a liquid, such as an imaging contrast agent, into the vascular system of a patient, because of the greater reliability and consistency in infusion rates and dosage when compared to a manual injector. The occurrence of blow-by in a syringe being actuated by a power injector is more deleterious that blow-by associated with a manual injection because the injection pressure can approach 1200 pounds per square inch (psi). However, blow-by has been noted for injection pressures as low as 50 psi. In addition to the uncertainties in patient dosage discussed above, the power injector itself can be damaged by the introduction of liquid into the mechanism or by the need to overdrive the motor to compensate for a reduced delivery rate. Further, the injector and the portion of the procedure room near the injector may be soiled by the escaped liquid. Still further, the sterility of the equipment may be compromised.

Thus, an improved plunger is needed for a syringe having a configuration of sealing flanges that will prevent blow-by of the liquid held within the syringe barrel during a dispensing procedure and that can do so without significantly increasing the sliding frictional force between the sealing flanges and the interior of the barrel.

SUMMARY OF THE INVENTION

The present invention addresses these and other problems by defining a plunger with dual sealing flanges for use with a syringe, where the plunger is configured to prevent a blow-by event. Further, the present invention provides a plunger configured with a pressure relief mechanism that preferentially ejects any liquid trapped between the sealing flanges of the plunger so as to prevent blow-by. The present invention provides sealing flanges with optimized dimensions or modified structure that eliminates blow-by without significantly altering the frictional force between the sealing flanges and the interior of the syringe barrel. Further, the present invention provides a plunger that is not sensitive to trapped liquid so that the more complex factors that contribute to the trapping of the liquid do not have to be addressed and solved.

According to the present invention, one embodiment of the plunger has a piston with a chamber susceptive of trapping a portion of the liquid when the plunger is in motion. When the plunger is moved by a dispensing force in a proximal-to-distal direction to dispense liquid from the syringe, the piston is configured to maintain a fluid-tight contact pressure with the interior surface of the syringe barrel and to preferentially exhaust any trapped liquid in a proximal direction.

In another embodiment, the piston has first and second spaced circumferential sealing flanges that project radially outwardly from a cylindrical outer surface. The second or proximal sealing flange is spaced from the first sealing flange to define a chamber, which may have an annular configuration. The first or distal sealing flange is substantially circumferentially continuous about the cylindrical outer surface of the plunger and has a barrel-contacting sealing surface that exerts a first contact pressure on the interior surface of the syringe barrel sufficient to normally maintain a fluid-tight seal therewith. The second sealing flange likewise has a barrel-contacting sealing surface configured to exhaust liquid trapped in the chamber in a proximal direction. The piston has a head, that is usually conical and integral with the cylindrical outer surface, that contacts the liquid held by the barrel and, according to one embodiment, that tapers to an included angle of about 120°.

According to one embodiment of the present invention, the second sealing flange may be substantially circumferentially continuous and exert a second contact pressure on the inside surface of the barrel that is lesser than the first contact pressure exerted by the first sealing flange. As a result, any liquid trapped in the chamber preferentially overcomes the second contact pressure and is exhausted in a proximal direction without disturbing the fluid-tight seal provided by the first sealing flange. The differential in contact pressure may be established by mismatching the radial distance of the sealing flanges, measured relative to the longitudinal axis of the barrel, so that the first sealing flange has a larger radial distance than the second sealing flange. Increasing the radial distance of the first sealing flange by 10 mils has been found to optimize the pressure relief without significantly altering the sliding frictional forces between the sealing flanges and the interior of the barrel.

In another embodiment, the second sealing flange is a circumferential sealing lip that projects in a radially outward and proximal direction from the cylindrical outer surface of the plunger. The sealing lip has a barrel-contacting sealing surface that contacts the inside flange of the syringe barrel. The sealing surface exerts a lesser contact pressure with the interior of the barrel than the first sealing flange and, as a result, the sealing lip can deflect proximally to exhaust any pressurized fluid trapped in the chamber between the sealing flanges without compromising the sealing ability of the first sealing flange.

In another embodiment, the plunger may comprise an outer sheath that surrounds the exterior of an inner member. The sheath includes first and second spaced circumferential sealing flanges that project radially outwardly from an exterior surface of a cylindrical sidewall for compressively engaging the interior of the syringe barrel.

In other embodiments, the contact pressure exerted by the second sealing flange may be reduced by removing a portion of the exterior of the piston or by removing a portion of the interior of the sheath that, in each case, is radially inwardly of the second sealing flange. The reduction in the contact pressure exerted by the second sealing flange against the interior of the barrel relative to the contact pressure of the first sealing flange provides a path of lesser resistance for pressurized trapped fluid to exhaust in a proximal direction.

The present invention shall become more apparent from the accompanying drawings and description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

DETAILED DESCRIPTION

The present invention is directed to plunger having dual sealing flanges for use with an otherwise conventional syringe, wherein the sealing flanges are configured to prevent pressurized liquid trapped between the sealing flanges from compromising the sealing ability of the plunger during a dispensing procedure. In particular, the plunger has a pressure relief mechanism, which is operable to preferentially eject any trapped liquid when a dispensing force is applied to the plunger. More particularly, one sealing flange is configured to have a reduced contact pressure with the interior of the syringe barrel. Pressurized trapped liquid is preferentially exhausted by this sealing flange without affecting the sealing ability of the plunger. As a result, the phenomenon known as blow-by is eliminated during a dispensing procedure. As used hereinafter, blow-by is defined as allowing a significant amount of liquid to leak past the sealing flanges of the plunger during a dispensing procedure.

Figure 1:
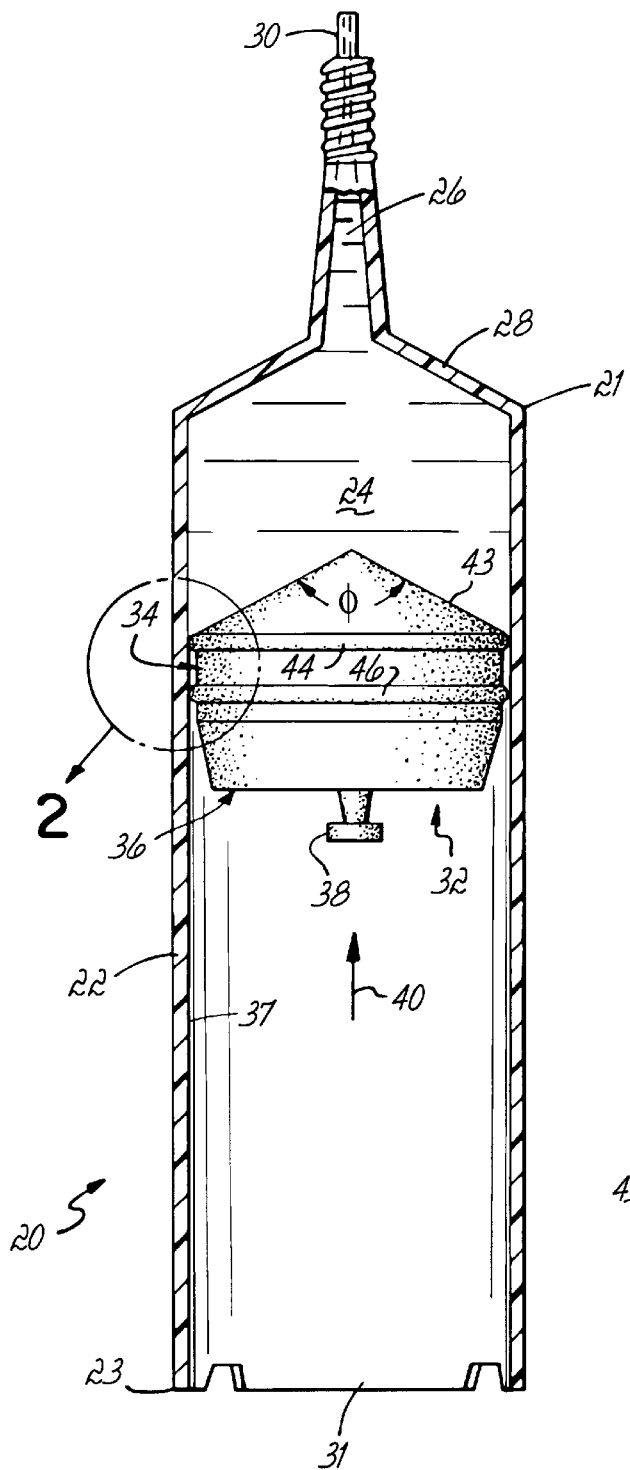
FIG. 1 is a side view of a plunger for a syringe, which is shown in longitudinal cross-section, according to the present invention.
Figure 2:
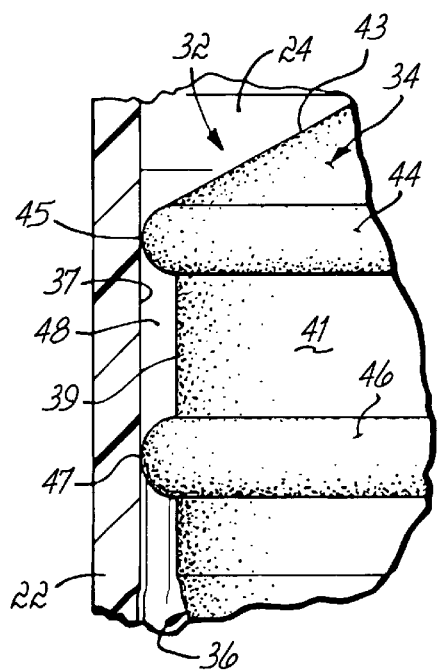
FIG. 2 is an enlarged view of encircled area "2" of FIG. 1.
Figure 3:
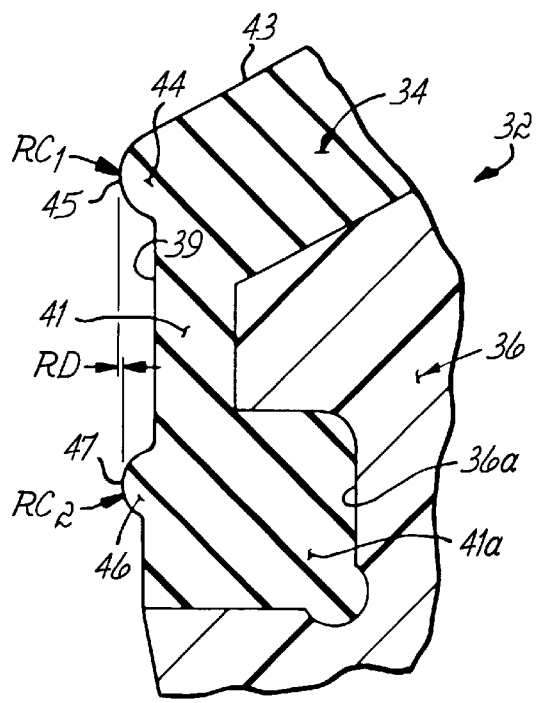
FIG. 3 is a section of the plunger shown in FIG. 2.

Referring to FIGS. 1–3, a syringe 20 includes an elongated, tubular barrel 22 extending along a longitudinal axis between a distal end 21 and a proximal end 23. A discharge outlet 26 is attached to a frustoconical portion 28 of distal end 21 and terminates with a discharge tip 30. Tip 30 is adapted to attach the interior of barrel 22 in fluid communication with a cannula or a Luer connector interfaced with a length of tubing and a catheter (not shown). Inserted through an access opening 31 in proximal end 23 of syringe 20 is a plunger 32, which comprises a piston-like structure positioned for sliding movement within the interior of barrel 22 and along a longitudinal axis thereof.

The portion of the interior of barrel 22 between tip 30 and plunger 32 defines a volume for containing a quantity of a liquid 24. This portion of the interior of barrel 22 may be either prefilled with liquid 24 or filled with liquid 24 by placing discharge outlet 26 in fluid communication with a liquid reservoir and moving plunger 32 in a proximal direction to siphon liquid 24 through discharge outlet 26. Alternatively, syringe 20 may be filled by pouring liquid 24 directly into the rear access opening 31 of barrel 22 and inserting the plunger 32. Syringe 20 may hold, for example, a maximum volume of 125 ml, 200 ml, etc. depending on the amount of liquid 24 to be delivered to the patient. It will be understood that the dimensions and capacity of syringe 20 may be varied without departing from the spirit and scope of the present invention.

Liquid 24 may comprise a substance suitable for injection into a patient, such as a pharmaceutical liquid or an imaging contrast agent. If liquid 24 is an imaging contrast agent, liquid 24 should be provided in barrel 22 with a quantity sufficient to facilitate an imaging operation.

The proximal side of the plunger 32 includes an attachment tab 38 adapted to couple plunger 32 with a gripper carried by a plunger ram (not shown). When a dispensing force of a sufficient magnitude is applied to the attachment tab 38 in a direction indicated by arrow 40, plunger 32 urges liquid 24 through outlet 26. In particular, syringe 20 may be configured for use with a power injector and the plunger ram may be attached to a power injector (not shown), for supplying the dispensing force to move plunger 32 within barrel 22.

As best shown in FIG. 3, one embodiment of the plunger 32 includes an outer sheath 34 having a cylindrical sidewall 41 and a conical head 43 integrally interconnected with the proximal end of sidewall 41. A substantial portion of conical head 43 contacts the liquid 24 contained within barrel 22. Conical head 43 has a predetermined included angle that, in the embodiment 10 shown in FIG. 1, tapers to an included angle, $\phi$, of about 120°. However, it is understood that other included angles may be selected without departing from the spirit and scope of the present invention. It is further understood that head 43 may have a geometrical shape other than that of a conical without departing from the spirit and scope of the present invention.

Sheath 34 is configured be received and held in a snug, resilient fit by an inner member 36. To that end, sheath 34 includes an annular ridge 41a extending about the interior of sidewall 41 and projecting in a radially inward direction. Annular ridge 41a engages an annular notch 36a provided on the exterior of inner member 36. Sheath 34 is formed of a low durometer elastomer, such as a natural rubber or an isoprene, and inner member 36 is formed of a higher durometer polymer, such as a delrin, a polycarbonate, or preferably a polypropylene.

A first sealing flange 44 and a second sealing flange 46 are circumferentially positioned about an outer surface 39 of sidewall 41. As best shown in FIGS. 2 and 3, sealing flanges 44, 46 are positioned in a spaced relationship and each projects radially outwardly from outer surface 39. Each sealing flange 44, 46 has a barrel-contacting sealing surface 45, 47, respectively, that compressively engages an interior surface 37 of barrel 22. The first sealing flange 44 is substantially circumferentially continuous and sealing surface 45 exerts a sufficient first contact pressure to normally provide a fluid-tight compressive engagement with the interior of barrel 22. First sealing flange 44 has a generally semi-circular cross-sectional profile with a predetermined radius of curvature $RC_1$ when in an uncompressed state. The second sealing flange 46 also has a substantially circumferentially continuous sealing surface 47 that exerts a second contact pressure on the interior of barrel 22. Second sealing flange 46 has a generally circular cross-sectional profile with a predetermined radius of curvature $RC_2$, when in an uncompressed state. The compressive engagement with the interior surface 37 deforms and distorts sealing surfaces 45, 47 such that, when plunger 32 is inserted into barrel 22, each of the sealing surfaces 45, 47 and the interior surface 37 is substantially coplanar. When plunger 32 is moved by a dispensing force in a proximal-to-distal direction, the frictional force between each of the sealing surfaces 45, 47 and the interior surface 37 of barrel 22 is determined by an appropriate coefficient of dynamic friction characteristic of the combination of respective materials and the radially outward force produced by the respective first or second contact pressure.

An annular chamber 48 is defined between the first and second sealing flanges 44, 46. Chamber 48 is an continuous, annular open volume disposed about the circumference of outer surface 39. It will be understood that chamber 48 may comprise multiple subchambers partitioned by sections of the outer surface 39 of cylindrical wall 41 without departing from the spirit and scope of the present invention. Annular chamber 48 is susceptible to trapping a portion of the liquid 24 that would otherwise reside in barrel 22, when plunger 32 is in motion.

In one embodiment of the present invention, the first and second flanges 44, 46 are configured to exhaust any trapped liquid 50 (FIG. 5) trapped by the annular chamber 48 in a distal-to-proximal direction toward access opening 31. Trapped liquid 50 is exhausted from chamber 48 without substantially disturbing the fluid-tight sealing ability of the first sealing flange 44. In particular, the sealing surface 47 of second sealing flange 46 exerts a contact pressure against the interior surface 37 of barrel 22 that is smaller than the contact pressure exerted by the sealing surface 45 of first sealing flange 44 against the interior surface 37 of barrel 22 when a dispensing force is applied to move plunger 32 in a proximal-to-distal direction for dispensing liquid 24 through the discharge outlet 26.

The relative contact pressures of the first and second sealing flanges 44, 46 may be controlled by adjusting their respective radial distances, measured with respect to the longitudinal axis of barrel 22. In particular the radial distance, measured relative to the longitudinal axis of barrel 22, of the first sealing flange 44 is adjusted to be greater than the radial distance of the second sealing flange 46. The difference in radial distance can be accomplished by mismatching the radius of curvature $RC_1$ and $RC_2$ of the sealing flanges 44 and 46, respectively. However, it is understood that the mismatch could be otherwise accomplished, such as by inserting a radial spacer between the curved portion of sealing flange 44 and outer surface 39, without departing from the spirit and scope of the present invention.

According to the present invention, the ability to exhaust trapped liquid 50 in a proximal direction toward access opening 31 is optimized by adjusting the radial distance of the second sealing flange 46 to be about 10 mils (0.010") less than the radial distance of the first sealing flange 44, when sealing flanges 44, 46 are in an uncompressed state. This 10 mil difference in radial distance RD (see FIG. 3) has been found to eliminate blow-by without significantly altering the dynamic frictional force between the sealing surfaces 45, 47 and the interior surface 37 of barrel 22.

By way of example, and not by way of limitation, a plunger 32 adapted for a syringe 20 having a capacity of 200 ml may have a first sealing flange 44 with a radial distance of about 0.951" and a second sealing flange 46 with a radial distance of about 0.9", wherein the radii of curvature $RC_1$, $RC_2$ of the respective sealing flanges 44, 46 are 20 mils and 30 mils, respectively. In this specific embodiment, sheath 34 has a side wall 45 with a radial distance of about 0.9135" and a wall thickness of about 80 mils to about 100 mils, preferably about 90 mils.

Figure 4:
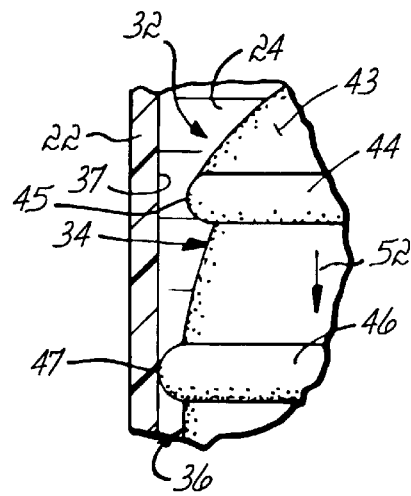
FIG. 4 is a view, similar to FIG. 2, during a filling operation.
Figure 5:
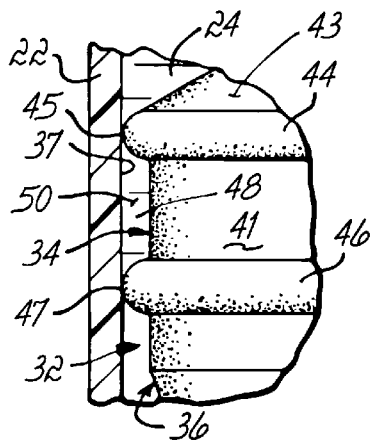
FIG. 5 is a view, similar to FIG. 4, following a filling operation.
Figure 6:
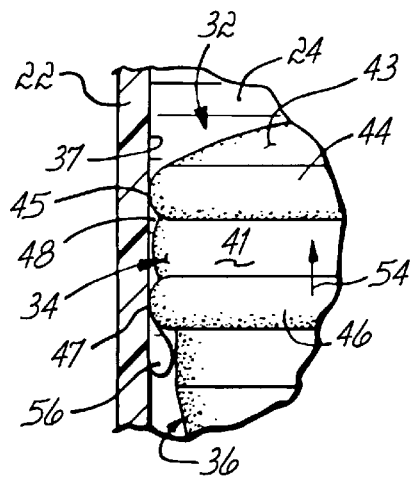
FIG. 6 is a view, similar to FIG. 5, during a dispensing procedure.

The operation of plunger 32 according to the present invention is diagrammatically illustrated in FIGS. 4–6. Referring to FIG. 4, the plunger 32 is moved in a proximal direction, indicated by arrow 52, to fill the barrel 22 with liquid 24 by aspiration during a filling operation. Under certain circumstances, the vacuum generated by the aspiration induces the barrel-contacting sealing surface 45 of first sealing flange 44 to lose contact with the interior surface 37 of barrel 22. A quantity of liquid 24 can pass between the first sealing flange 44 and interior surface 37 of barrel 22 and become trapped in annular chamber 48, as shown in FIG. 5. Alternatively, trapped fluid 50 can originate from canting of the plunger 32 during a dispensing procedure if either the attachment tab 38 is slightly off-center or the frictional force between the sealing flanges 44, 46 and the interior surface 37 of barrel 22 is circumferentially nonuniform.

As shown in FIG. 6, if a quantity of trapped liquid 50 otherwise sufficient to produce blow-by during a dispensing procedure becomes trapped in annular chamber 48, the reduced contact pressure between the sealing surface 47 of the second sealing flange 46 and the interior surface 37 of the barrel 22 permits all or a portion of the trapped liquid 50 to pass as in a proximal direction when a dispensing force is applied to plunger 32. As plunger 32 is advanced by the dispensing force in a distal direction, indicated by arrow 54, the liquid 24 in barrel 22 exerts a hydrostatic pressure on the conical head 43 of sheath 34. The hydrostatic pressure axially compresses the sheath 34 so that cylindrical sidewall 41 distends radially outwardly toward the interior surface 37 of barrel 22. As a result, the volume of annular chamber 48 is reduced and any trapped fluid 50 is pressurized.

The axial compression increases the contact pressure exerted on the interior surface 37 of barrel 22 by sealing surface 45 of the first sealing flange 44, which is urged radially outwardly in proportion to the hydrostatic pressure. The axial compression also increases the contact pressure exerted on the interior surface 37 of barrel 22 by sealing surface 47 of the second sealing flange 46, which is urged radially outwardly in proportion to the hydrostatic pressure.

Due to the difference in radial distance RD, sealing surface 47 of the second sealing flange 46 exerts a weakened contact pressure against the interior surface 37 of barrel 22 relative to the contact pressure exerted by the first sealing flange 44. As a result, sealing surface 47 may preferentially lose contact with the interior of barrel 22 so that all or a portion of the pressurized trapped liquid 50 can be exhausted in a proximal direction as exhausted fluid 56. However, the contact pressure exerted by sealing surface 45 of the first sealing flange 44 against the interior surface 37 of barrel 22 is not significantly effected by the trapped fluid 50. Sealing surface 45 remains compressively engaged against the interior surface 37 of barrel 22 with a contact pressure sufficient to resist leakage of fluid 24.

Figure 7:
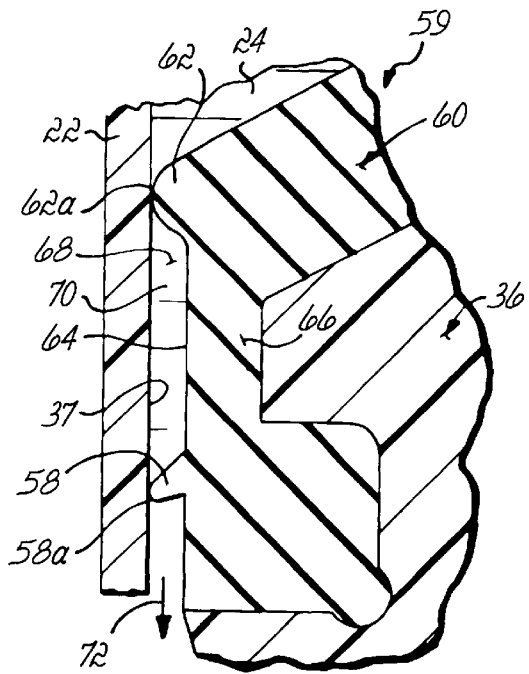
FIG. 7 is a section view of an alternative embodiment of a plunger for a syringe according to the present invention.

According to the present invention, an alternative embodiment of a plunger 59 having a sheath 60 covering an inner member 36 is presented in FIG. 7 in which like parts have like numerals as in FIGS. 1–3. Sheath 60 may carry a circumferential lip 58 having a spaced relationship with respect to a generally semi-circular sealing flange 62. Sealing flange 62 has a barrel-contacting sealing surface 62a that compressively engages the interior surface 37 of barrel 22 with a contact pressure sufficient to establish a fluid-tight engagement during a dispensing procedure. Circumferential lip 58 projects in a radially outwardly and proximal direction from an outer surface 64 of a cylindrical sidewall 66. A contact portion 58a of lip 58 contacts the interior surface 37 of the barrel 22, with a contact pressure. During a dispensing operation with a sufficient amount of a trapped liquid 68 confined in an annular chamber 70 between lip 58 and sealing flange 62, the proximally-directed force exerted by trapped liquid 68 deflects lip 58 in a distal-to-proximal direction indicated by arrow 72 on FIG. 7, so that contact portion 58a loses contact with the interior surface 37 of barrel 22 to create a gap therebetween. All or a portion of the trapped liquid 68 flows through the gap and past the deflected lip 58 in a proximal direction toward the access opening 31 (FIG. 1).

Figure 8:
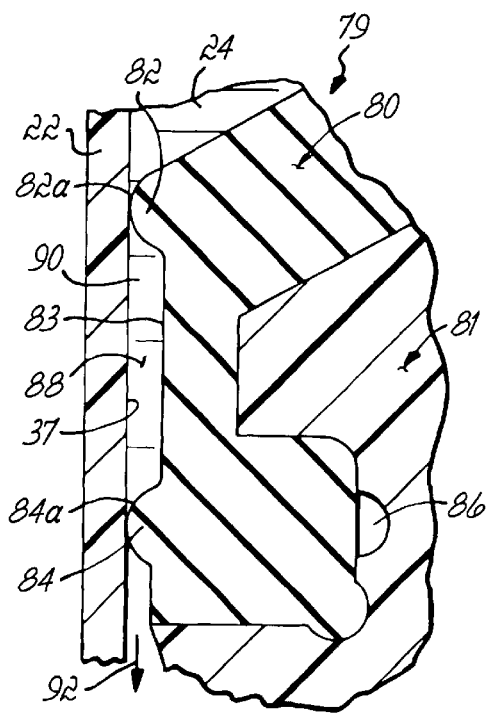
FIG. 8 is a section view of another alternative embodiment of a plunger for a syringe according to the present invention.

In accordance with the present invention, a plunger 79 having a sheath 80 covering an inner member 81 is presented in FIG. 8 in which like parts have like numerals as in FIGS. 1–3. An outer surface 83 of sheath 80 carries a first sealing flange 82 and a second sealing flange 84, which have barrel-contacting sealing surfaces 82a, 84a, respectively. An annular chamber 90 is defined in the space bounded by the sealing flanges 82, 84, the interior surface 37 of barrel 22, and the outer surface 83 of sheath 80. The contact pressure exerted by the sealing surface 84a of the second sealing flange 84 against the interior surface 37 of barrel 22 is reduced, relative to the contact pressure exerted by sealing surface 82a, by removing material from the exterior of inner member 81. Specifically, material is removed at a location beneath the second sealing flange 84 to provide an annular recess 86 of a semi-circular cross-sectional profile positioned radially inward from the second sealing flange 84. It is understood that the shape or size of recess 86 may be varied without departing from the spirit and scope of the present invention. For example, recess 86 may have a rectangular cross-sectional profile, rather than the semi-circular cross-sectional profile illustrated in FIG. 8.

During a dispensing procedure with a sufficient quantity of a pressurized trapped fluid 88 trapped in annular chamber 90, second sealing flange 84 will preferentially yield under the force applied by trapped fluid 88. As a result, the trapped fluid 88 will exhaust in a proximal direction, as indicated by arrow 92, through the gap created between the sealing surface 84a of the second sealing flange 84 and the interior surface 37 of barrel 22. Sealing surface 86a will remain compressively engaged against the interior surface 37 of barrel 22 with a contact pressure sufficient to resist the hydrostatic pressure exerted in a proximal direction by liquid 24 held by barrel 22.

Figure 9:
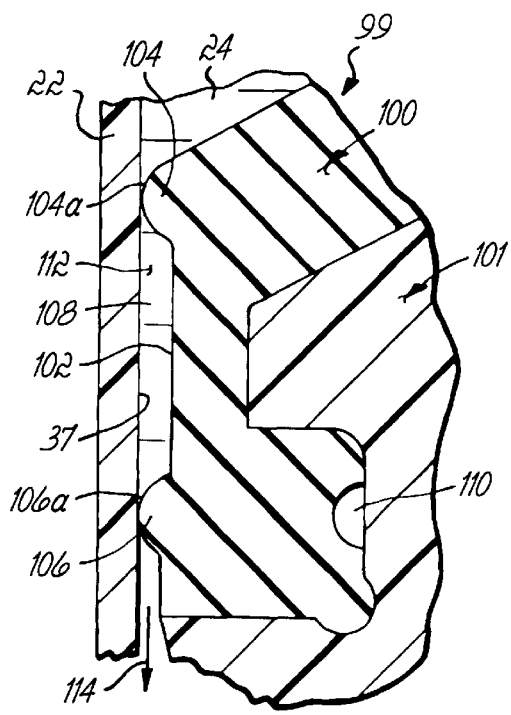
FIG. 9 is a section view of yet another alternative embodiment of a plunger for a syringe according to the present invention.

In accordance with the present invention, a plunger 99 having a sheath 100 covering an inner member 101 is presented in FIG. 9 in which like parts have like numerals as in FIGS. 1–3. An outer surface 102 of sheath 100 carries a first sealing flange 104 and a second sealing flange 106 having respective barrel-contacting sealing surfaces 104a, 106a. An annular chamber 108 is defined in the space bounded by the sealing flanges 104, 106, the interior surface 37 of barrel 22, and the outer surface 102 of sheath 100. Material is removed from the interior of sheath 100 radially inward from the second sealing flange 106 to provide an annular recess 110. Recess 110 functions to reduce the contact pressure that the sealing surface 106a of second sealing flange 106 exerts against the interior surface 37 of barrel 22. It is understood that the shape or size of recess 110 may be varied without departing from the spirit and scope of the present invention. For example, recess 110 may have a rectangular cross-sectional profile, rather than the semicircular cross-sectional profile illustrated in FIG. 9.

During a dispensing procedure, second sealing flange 106 will preferentially yield under the force applied by pressurized trapped fluid 112, if trapped fluid 112 is present in a sufficient quantity in annular chamber 108. As a result, the trapped fluid 112 will exhaust in a proximal direction, as indicated by arrow 114 on FIG. 9, through the gap created between the sealing surface 106a of second sealing flange 106 and the interior surface 37 of barrel 22. Barrel-contacting sealing surface 104a of first sealing flange 104 will remain compressively engaged against the interior surface 37 of barrel 22 with a contact pressure sufficient to resist the hydrostatic pressure exerted proximally by liquid 24 within barrel 22.

Figure 10:
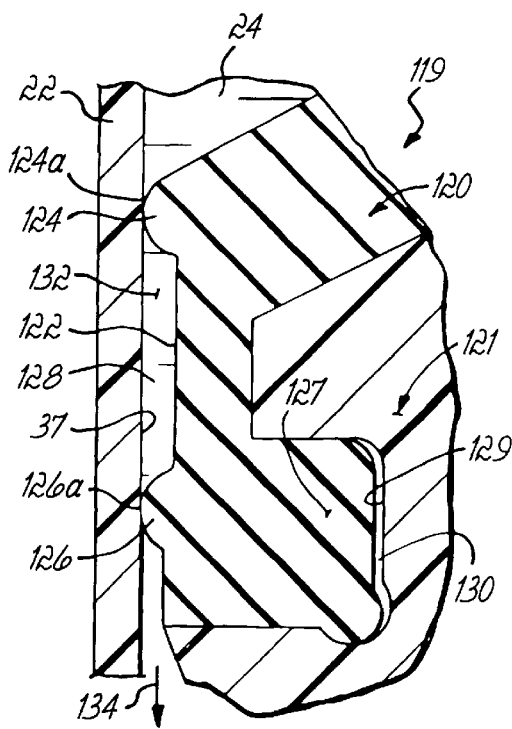
FIG. 10 is a section view of an alternative embodiment of the plunger shown in FIG. 8.

In accordance with the present invention, a plunger 119 having a sheath 120 covering an inner member 121 is presented in FIG. 10 in which like parts have like numerals as in FIGS. 1–3. An outer surface 122 of sheath 120 carries a first sealing flange 124 and a second sealing flange 126 in a spaced relationship and having respective barrel-contacting sealing surfaces 124a, 126a. An annular chamber 128 is defined in the space bounded longitudinally by the sealing flanges 124, 126, and bounded radially between the interior surface 37 of barrel 22 and the outer surface 122 of sheath 120. An annular ridge 127 on the interior of sheath 120 engages an annular notch 129 provided on the exterior of inner member 121 for securing sheath 120 to inner member 121.

An annular recess 130 is positioned radially inward of second sealing flange 126 and provides a circumferential cavity that separates annular notch 129 and annular ridge 127. Recess 130 is created by removing material from either sheath 120 to increase the inner radial distance of annular ridge 127 or, in the alternative, by removing material from inner member 121 to reduce the outer radial distance of the annular notch 129. It is understood that the shape or size of recess 130 may be varied without departing from the spirit and scope of the present invention.

During a dispensing procedure, recess 130 functions to reduce the contact pressure exerted by the barrel-contacting sealing surface 126a of second sealing flange 126 against the interior surface 37 of barrel 22. Recess 130 permits annular ridge 127 to move radially inward in response to the axial compression of sheath 120. As a result, sealing surface 126a of second sealing flange 126 will preferentially yield under the force applied by pressurized trapped fluid 132, if a sufficient quantity of trapped fluid 132 is present in annular chamber 128. Trapped fluid 132 exhausts in a proximal direction, as indicated by arrow 134 on FIG. 10, through the gap created between sealing surface 126a and the interior surface 37 of barrel 22. Barrel-contacting sealing surface 124a of first sealing flange 124 will remain compressively engaged against the interior surface 37 of barrel 22 with a contact pressure sufficient to resist the hydrostatic pressure exerted proximally by liquid 24 within barrel 22.

While the present invention has been illustrated by the description of embodiments thereof, and while the embodiments have been described in considerable detail, they are not intended to restrict or in any way limit the scope of the appended claims to such detail. Additional advantages and modifications will readily appear to those skilled in the art. For example, the present invention is not limited to dispensing pharmaceutical liquids and may be used in conjunction with a syringe for dispensing non-pharmaceutical liquids, such as adhesives. The invention in its broader aspects is therefore not limited to the specific details, representative apparatus and method and illustrative examples shown and described. Accordingly, departures may be made from such details without departing from the scope or spirit of applicant's general inventive concept.

What is claimed is:

1. A plunger for use with a syringe having a barrel filled with a liquid that exerts a fluid pressure on the plunger when the plunger is in motion, the barrel having a cylindrical wall with an interior surface and a longitudinal axis extending between a proximal end and a distal end, a discharge outlet at the distal end through which the liquid passes when dispensed, and an access opening at the proximal end for applying a dispensing force to move the plunger in a proximal-to-distal direction toward the discharge outlet, said plunger comprising:

a piston operably mounted within the syringe barrel for dispensing the liquid from the discharge outlet, said piston including a chamber susceptive of trapping a portion of the liquid when the piston is in motion, said piston having a circumferential first sealing flange exerting a fluid-tight contact pressure with the interior surface of the syringe barrel distally of the chamber and a circumferential second sealing flange exerting a lesser contact pressure with the interior surface of the syringe barrel proximally of the chamber to allow the portion of the liquid trapped in the chamber to be exhausted between the second sealing flange and the interior surface in a proximal direction when the dispensing force is applied to said piston in a proximal-to-distal direction for dispensing liquid from the barrel through the distal discharge outlet, so that the fluid-tight seal between said first sealing flange and the interior surface is undisturbed.

2. The plunger of claim 1, wherein said chamber has the shape of an annulus and is disposed between said first and second sealing flanges.

3. The plunger of claim 1, wherein said first sealing flange has a radially outermost barrel-contacting sealing surface located at a first predetermined radial distance from the longitudinal axis of the barrel and said second sealing flange has a radially outermost barrel-contacting sealing surface of a lesser second predetermined radial distance from the longitudinal axis of the barrel.

4. The plunger of claim 3, wherein said second predetermined radial distance is about 10 mils less than said first predetermined radial distance.

5. The plunger of claim 3, wherein said first and second sealing flanges have generally circular cross-sectional profiles when in an uncompressed state.

6. The plunger of claim 5, wherein said second predetermined radial distance is about 10 mils less than said first predetermined radial distance.

7. The plunger of claim 3, wherein said second sealing flange comprises a circumferential sealing lip projecting in a radially outward and proximal direction from a cylindrical outer surface of said piston, said lip having a barrel-contacting sealing surface that contacts the interior surface of the syringe barrel such that said lip deflects proximally to exhaust liquid trapped in said chamber.

8. The plunger of claim 7, wherein said first sealing flange has a generally circular cross-sectional profile of a first predetermined radius, when in an uncompressed state.

9. The plunger of claim 1, wherein said piston further includes a cylindrical outer surface and a conical head that is positioned proximal of said outer surface and is integral with said outer surface, wherein a substantial portion of said conical head is in contact with the liquid in the barrel.

10. The plunger of claim 9, wherein said conical head tapers to an included angle of about 120°.

11. The plunger of claim 1, wherein the piston further comprises an inner member and a sheath surrounding an exterior surface of said inner member, said sheath including a cylindrical sidewall and said first and second sealing flanges project radially outwardly from an exterior surface of said sidewall, wherein said second sealing flange is spaced proximally of said first sealing flange so as to define therebetween said chamber.

12. The plunger of claim 11, wherein the exterior surface of said inner member is at least partially removed radially inwardly of said second sealing flange.

13. The plunger of claim 11, wherein the sidewall of said sheath has an interior surface that is at least partially removed radially inwardly of said second sealing flange.

14. The plunger of claim 11, wherein said sidewall and said first and second sealing flanges have an integral, one-piece configuration.

15. The plunger of claim 11, wherein said sheath further includes a conical head that is integral with said sidewall, wherein a substantial portion of said conical head contacts the liquid within the barrel.

16. The plunger of claim 15, wherein said conical head tapers to an included angle of about 120°.

17. The plunger of claim 11, wherein said chamber has the shape of an annulus.

18. The plunger of claim 11, wherein said second sealing flange is substantially circumferentially continuous and exerts a second contact pressure on the interior surface of the barrel lesser than the first contact pressure exerted by said first sealing flange, so that any liquid trapped in said annular chamber is exhausted in a proximal direction without disturbing the fluid-tight seal of said first sealing flange.

19. The plunger of claim 11, wherein said first sealing flange has a radially outermost barrel-contacting sealing surface located at a first predetermined radial distance from the longitudinal axis of the barrel and said second sealing flange has a radially outermost barrel-contacting sealing surface of a lesser second predetermined radial distance from the longitudinal axis of the barrel.

20. The plunger of claim 19, wherein sad second predetermined radial distance is about 10 mils less than said first predetermined radial distance.

21. The plunger of claim 19, wherein said first and second sealing flanges have generally circular cross-sectional profiles when in an uncompressed state.

22. The plunger of claim 21, wherein said second predetermined radial distance is about 10 mils less than said first predetermined radial distance.

23. The plunger of claim 11, wherein said second sealing flange comprises a circumferential sealing lip projecting in a radially outward and proximal direction from said exterior surface of said cylindrical sidewall, said sealing lip having a barrel-containing sealing portion that contacts the interior surface of the barrel such that said lip deflects proximally to exhaust liquid trapped in said chamber.

24. The plunger of claim 23, wherein said first sealing flange has a generally circular cross-sectional profile of a first predetermined radius when in an uncompressed state.

25. A sheath for attachment to the exterior of an inner member to provide a syringe plunger, the sheath for providing a sealing engagement an the interior surface of a syringe barrel that has a longitudinal axis with a distal end and a proximal end, a distal discharge opening for dispensing a liquid held by the barrel, and a longitudinal axis, the sheath comprising:

a cylindrical sidewall having an exterior surface, a proximal end and a distal end;

a head that is integral with the distal end of the sidewall, wherein said sidewall and said head are configured for receiving the exterior of the inner member in a snug fit;

a first circumferential sealing flange projecting radially outwardly from said exterior surface of said sidewall, said first sealing flange being substantially circumferentially continuous and exerting a sufficient first contact pressure on the interior surface of the syringe barrel to maintain a fluid-tight seal therewith; and a second circumferential sealing flange projecting radially outwardly from the exterior surface of the sidewall, said second sealing flange in a spaced position proximally of the first sealing flange so as to define therebetween a chamber susceptive of trapping a portion of the liquid when the piston is in motion, wherein said second sealing flange exerts a second contact pressure lesser than the first contact pressure of the first sealing flange that permits any liquid trapped in the chamber to be exhausted between the second sealing flange and the interior surface in a proximal direction when a dispensing force is applied to the syringe plunger to move the plunger for dispensing liquid from the barrel through the distal discharge outlet, so that the fluid-tight seal between said first sealing flange and the interior surface is undisturbed.

26. The sheath of claim 25, wherein said chamber has the shape of an annulus.

27. The sheath of claim 25, wherein said first sealing flange has a radially outermost barrel-contacting sealing surface located at a first predetermined radial distance from the longitudinal axis of the barrel and said second sealing flange has a radially outermost barrel-contacting sealing surface of a lesser second predetermined radial distance from the longitudinal axis of the barrel.

28. The sheath of claim 27, wherein said second predetermined radial distance is about 10 mils less than said first predetermined radial distance.

29. The sheath of claim 28, wherein said first and second sealing flanges have generally circular cross-sectional profiles when in an uncompressed state.

30. The sheath of claim 29, wherein said second predetermined radial distance is about 10 mils less than said first predetermined radial distance.

31. The sheath of claim 25, wherein said second sealing flange comprises a circumferential sealing lip projecting in a radially outward and proximal direction from said exterior surface of said cylindrical sidewall, said sealing lip having a barrel-containing sealing surface that contacts the interior surface of the syringe barrel such that said lip deflects proximally to exhaust liquid trapped in said chamber.

32. The sheath of claim 31, wherein said first sealing flange has a generally circular cross-sectional profile of a first predetermined radius when in an uncompressed state.

33. The sheath of claim 25, wherein said head is a conical head.

34. The sheath of claim 33, wherein said conical head tapers to an included angle of about 120°.

35. A syringe for dispensing a liquid when acted upon by a dispensing force, said syringe comprising:

a tubular barrel having a cylindrical wall with a proximal end, a distal end, a longitudinal axis, an interior surface, a proximal access opening, and a distal discharge outlet, wherein the barrel is adapted for holding a liquid; and a plunger operably mounted within the barrel for dispensing the liquid from the discharge opening, said plunger including a chamber susceptive of trapping a portion of the liquid when the plunger is in motion, said plunger having a circumferential first sealing flange exerting a fluid-tight contact pressure with the interior surface of the tubular barrel distally of the chamber and a circumferential second sealing flange exerting a lesser contact pressure with the interior surface of the syringe barrel proximally of the chamber to allow the portion of the liquid trapped in the chamber to be exhausted between the second sealing flange and the interior surface in a proximal direction when the dispensing force is applied to said piston in a proximal-to-distal direction for dispensing liquid from the barrel through the distal discharge outlet, so that the fluid-tight seal between said first sealing flange and the interior surface is undisturbed.

36. The syringe of claim 35, wherein said chamber has the shape of an annulus and is disposed between said first and said second sealing flanges.

37. The syringe of claim 35, wherein said first sealing flange has a radially outermost barrel-contacting sealing surface located at a first predetermined radial distance from the longitudinal axis of the barrel and said second sealing flange has a radially outermost barrel-contacting sealing surface of a lesser second predetermined radial distance from the longitudinal axis of the barrel.

38. The syringe of claim 37, wherein said second predetermined radial distance is about 10 mils less than said first predetermined radial distance.

39. The syringe of claim 37, wherein said first and second sealing flanges have generally circular cross-sectional profiles when in an uncompressed state.

40. The syringe of claim 39, wherein said second predetermined radial distance is about 10 mils less than said first predetermined radial distance.

41. The syringe of claim 35, wherein said second sealing flange comprises a circumferential sealing lip projecting in a radially outward and proximal direction from an outer surface of said plunger, said lip having a barrel-contacting sealing surface that contacts the interior surface of the syringe barrel such that said lip deflects proximally to exhaust liquid trapped in said chamber.

42. The syringe of claim 41, wherein said first sealing flange has a generally circular cross-sectional profile of a first predetermined radius when in an uncompressed state.

43. The syringe of claim 35, wherein said plunger further includes a conical head that is integral with said sidewall.

44. The syringe of claim 43, wherein said conical head tapers to an included angle of about 120°.

45. The syringe of claim 35, wherein the plunger further comprises an inner member and a sheath surrounding the exterior surface of said inner member, said sheath including a cylindrical sidewall and said first and second sealing flanges project radially outwardly from an exterior surface of said sidewall, wherein said second sealing flange is spaced proximally of the first sealing flange so as to define the chamber therebetween.

46. The syringe of claim 45, wherein the exterior surface of said inner member is at least partially removed radially inwardly of said second sealing flange.

47. The syringe of claim 45, wherein the sidewall of said sheath has an interior surface that is at least partially removed radially inwardly of said second sealing flange.

48. The syringe of claim 45, wherein said sidewall and said circumferential sealing flanges have an integral, one-piece configuration.

49. The syringe of claim 45, wherein said sheath further includes a head that is integral with said sidewall, said head in contact with said liquid, wherein a substantial portion of said conical head contacts the liquid within the barrel.

50. The syringe of claim 49, wherein said head is conical and tapers to an included angle of about 120°.

51. The syringe of claim 45, wherein said chamber has the shape of an annulus.

52. The syringe of claim 45, wherein said second sealing flange being substantially circumferentially continuous and exerting a second contact pressure on said inside surface of the barrel lesser than the first contact pressure exerted by said first sealing flange, so that any liquid trapped in the annular chamber is exhausted in a proximal direction without disturbing the fluid-tight seal of said first sealing flange.

53. The syringe of claim 45, wherein said first sealing flange has a radially outermost barrel-contacting sealing surface located at a first predetermined radial distance from the longitudinal axis of the barrel and said second sealing flange has a radially outermost barrel-contacting sealing surface of a lesser second predetermined radial distance from the longitudinal axis of the barrel.

54. The syringe of claim 53, wherein said second predetermined radial distance is about 10 mils less than said first predetermined radial distance.

55. The syringe of claim 53, wherein said first and second sealing flanges have generally circular cross-sectional profiles when in an uncompressed state.

56. The syringe of claim 55, wherein said second predetermined radial distance is about 10 mils less than said first predetermined radial distance.

57. The syringe of claim 52, wherein said second sealing flange comprises a circumferential sealing lip projecting in a radially outward and proximal direction from said exterior surface of said cylindrical sidewall, said lip having a barrel-contacting sealing surface that contacts the inside surface of the syringe barrel such that said lip deflects proximally to exhaust liquid trapped in said chamber.

58. The syringe of claim 57, wherein said first sealing flange has a generally circular cross-sectional profile of a first predetermined radius when in an uncompressed state.

59. The syringe of claim 35, further comprising a quantity of a liquid within said tubular barrel, said liquid suitable for injection into a patient.

60. The syringe of claim 59, wherein said liquid is an imaging contrast agent and the quantity of imaging contrast agent is sufficient to facilitate an imaging operation.

61. A method for dispensing a liquid imaging medium with a dispensing force, the method comprising:

providing a syringe barrel having a forward end with a discharge outlet, an interior surface and an open rearward end;

providing a plunger within said syringe barrel, said plunger including a chamber susceptive of trapping a portion of a liquid present in the syringe barrel when the plunger is in motion and said plunger located forward of the chamber and having a first circumferential sealing flange configured to normally provide a first contact pressure with said interior surface of the syringe barrel, and a second sealing flange located rearward of the chamber and configured to provide a lesser second contact pressure of a fluid-tight magnitude with said interior surface of the syringe barrel, wherein said second sealing flange preferentially exhausts trapped liquid imaging medium from the chamber in a rearward direction when a dispensing force is applied to said piston for dispensing liquid from the barrel through the discharge outlet;

filling the syringe barrel forward of the plunger with a quantity of a liquid imaging medium;

connecting the syringe to a patient via a catheter and a tube interconnecting catheter and the discharge outlet of the syringe barrel; and applying a dispensing force to the plunger for dispensing liquid imaging medium from the syringe into the patient, wherein liquid imaging medium trapped in the chamber is preferentially exhausted between the second sealing flange and said interior surface in a rearward direction due to the lesser contact pressure exerted by the second sealing flange against the interior surface of the syringe barrel.

62. The method of claim 61 wherein the step of filling the syringe barrel with a quantity of liquid imaging medium occurs before the step of providing the plunger.

63. The method of claim 61 wherein the step of filling the syringe barrel with a quantity of liquid imaging medium occurs after the step of providing the plunger, and the step of filling comprises placing the outlet opening in fluid communication with a reservoir of liquid imaging medium and siphoning the liquid imaging medium through the outlet opening by moving the plunger in a rearward direction within the syringe barrel.

* * * * *

UNITED STATES PATENT AND TRADEMARK OFFICE
CERTIFICATE OF CORRECTION

PATENT NO. : 6,511,459 B1
DATED : January 28, 2003
INVENTOR(S) : Fago, Frank M.

It is certified that error appears in the above-identified patent and that said Letters Patent is hereby corrected as shown below:

Column 2,
Line 34, reads "dispensed in an precise" and should read -- dispensed in a precise --.
Line 47, reads "deleterious that blow-by" and should read -- deleterious than blow-by --.

Column 4,
Line 53, reads "directed to plunger" and should read -- directed to a plunger --

Column 5,
Line 53, reads "embodiment 10 shown in" and should read -- embodiment shown in --.
Line 58, reads "than that of a conical" and should read -- than that of conical --.
Line 60, reads "configured be received" and should read -- configured to be received --.

Column 6,
Line 35, reads "is an continuous" and should read -- is a continuous --.

Column 7,
Line 19, reads "0.9", wherein" and should read -- 0.941", wherein --.

Column 8,
Line 8, reads "significantly effected" and should read -- significantly affected --.

Column 12,
Lines 5 and 67, reads "barrel-containing sealing" and should read -- barrel-contacting sealing --.
Line 13, reads "engagement an the interior" and should read -- engagement on the interior --.

Signed and Sealed this

Fifteenth Day of July, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,511,459 B1
DATED         : January 28, 2003
INVENTOR(S)   : Fago It is certified that error appears in the above-identified patent and that said Letters Patent is hereby corrected as shown below:

Title page,
Item [*] Notice, delete the phrase "by 16 days" and insert -- by 17 days --

Signed and Sealed this

Eighteenth Day of May, 2004

JON W. DUDAS
*Acting Director of the United States Patent and Trademark Office*